United States Patent [19]
Reis et al.

[11] 4,263,118
[45] Apr. 21, 1981

[54] DISINFECTION DEVICE

[75] Inventors: August K. Reis, Faistenbergerstr. 1, 8000 München 90, Fed. Rep. of Germany; Norbert L. Kirmaier, Aschheim; Meinolf H. A. Schöberl, Prien, both of Fed. Rep. of Germany

[73] Assignee: August K. Reis, Munich, Fed. Rep. of Germany

[21] Appl. No.: 117,811

[22] Filed: Feb. 1, 1980

[30] Foreign Application Priority Data

Jul. 18, 1979 [DE] Fed. Rep. of Germany ....... 2929043

[51] Int. Cl.³ .................. C25B 9/02; C25B 11/03; C25B 11/04
[52] U.S. Cl. .................. 204/242; 204/279; 204/284; 204/286; 204/292; 204/275
[58] Field of Search .............. 204/242, 275, 286, 288, 204/289, 284, 292, 149, 268, 248–249, 297 R, 279

[56] References Cited

U.S. PATENT DOCUMENTS

| | | | |
|---|---|---|---|
| 2,816,067 | 12/1957 | Keidel | 204/242 X |
| 3,888,756 | 6/1975 | Teshima et al. | 204/275 |
| 3,893,900 | 7/1975 | Teshima et al. | 204/149 X |
| 3,900,377 | 8/1975 | Enns et al. | 204/149 |
| 3,972,795 | 8/1976 | Goens et al. | 204/275 X |
| 4,140,616 | 2/1979 | Wheatley et al. | 204/286 X |
| 4,160,711 | 7/1979 | Nishizawa et al. | 204/149 X |

Primary Examiner—T. Tung
Assistant Examiner—D. R. Valentine
Attorney, Agent, or Firm—Donald Brown

[57] ABSTRACT

A disinfection device has a plurality of electrodes arranged in planes, the electrodes in the planes being conductively connected by conductive and non-conductive carrier elements at their opposite ends. The elements alternate on opposed walls of the housing and fit together by reason of projections and corresponding recesses on the conductive and non-conductive elements. The electrodes may be, in certain embodiments, of expanded metal or sintered metal.

5 Claims, 5 Drawing Figures

DISINFECTION DEVICE

The invention relates to a disinfection device for disinfecting a liquid, in particular though not exclusively water, by electrochemical treatment.

More particularly the invention relates to a device of the type having a plurality of electrodes, each contained in one of a plurality of planes which are successively arranged in the sense of liquid flow through the device and each plane containing a plurality of electrodes which are conductively connected. The planes are insulated from one another.

In such a device the electrodes must each be built into the housing of the device and must be connected to a voltage supply. It has already been proposed to connect the electrodes of each particular plane at one end by means of respective spacers or carrier elements which are of rectangular shape and have mutually parallel edges so that the spaces of the different planes can be stacked one above the other.

It is the object of the invention to provide an improved disinfection device of the above type which can be assembled in a particularly simple manner. A further object is to provide electrodes which allow a higher efficiency of disinfection.

According to the present invention there is provided a disinfection device comprising a housing defined by walls, and a plurality of electrodes arranged in planes, conductive carrier elements supporting and electrically interconnecting the elements of the planes at one end, non-conductive carrier elements supporting the elements of the plane at the other end, the conductive and non-conductive carrier elements being alternately provided along opposed walls of the housing, the edges of the conductive carrier elements having projecting zones with sides at an angle to the plane of the corresponding electrodes, the edges of the non-conductive carrier elements having recesses which correspond to and receive the projections on the conductive carrier elements.

Further features and advantages of the invention can be appreciated from the following description given by way of example only with reference to the accompanying drawings in which.

Figure 1:
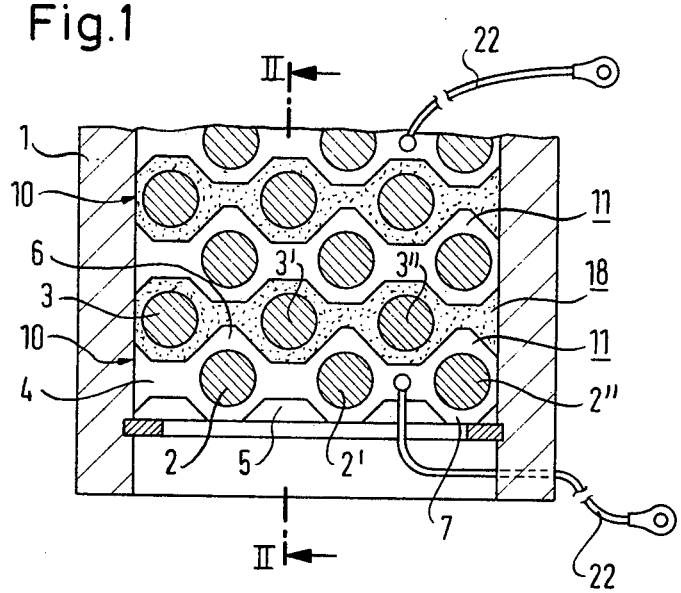
FIG. 1 shows a part of a disinfection device of the invention, in section along the line I—I of FIG. 2, the side wall being omitted.
Figure 2:
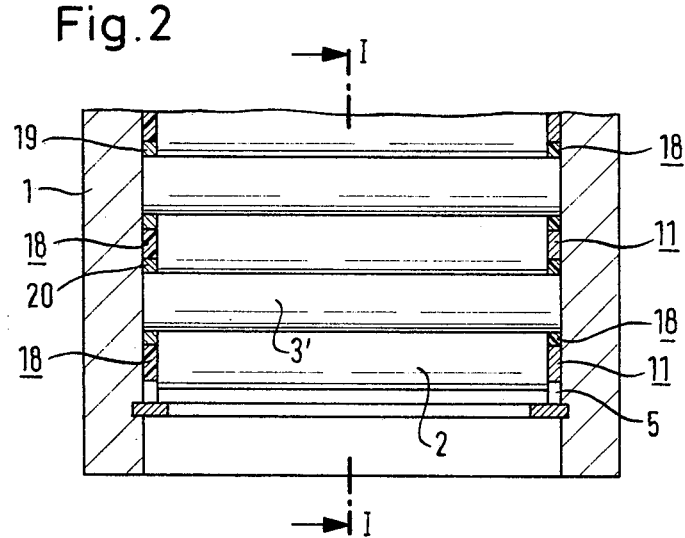
FIG. 2 shows the reactor shown in FIG. 1, in a sectional representation along the line II—II in FIG. 1.

In the reactor shown in FIGS. 1 and 2, sets of electrode rods such as 2, 2', 2" and 3, 3', 3" are arranged in planes within a generally rectangular housing. The rods are connected at one end of the sets by means of a respective conductive carrier element 11 and on the opposite end face by means of a respective insulating carrier element 18. The carrier elements abut walls 1 of the device, and the conductive connections of the successive sets are at alternate walls, with insulating connections between each pair of conductive connections at each wall. At the left wall in FIG. 2 conductive carrier elements are marked 19 and 20. As can best be seen in FIG. 1, each carrier element has edges only parts of which are parallel to the plane of the electrodes. In the illustrative embodiment shown, the edges of the conductive elements 11 in the intermediate zones between adjacent electrodes have quadrangular recesses 5 between portions 6, 7 which project respectively upwards and downwards. The upper edge of the element 11 is formed asymmetrically about the centre lines of the electrodes relative to the lower edge so that the upwardly projecting portion 6 is, as measured from that line, greater than the downwardly projecting portion 7. Moreover, the conductive carrier element 11 is also formed asymmetrically about the mid point of its length such that near one end there is a narrowed zone 4 which is not present at the other end. The insulating carrier elements 18, which are between the conductive carrier elements, are also of asymmetrical construction and are entirely congruent with the carrier elements 11. The lower edges of elements 18 differ from the lower edges of the conductive carrier elements in that the lower quadrangular recesses are deeper than the corresponding upper quadrangular recesses, and in particular to the same extent as the upper projecting portions 6 of elements 11 are higher than the lower projecting portions 7. The result of this is that, on assembling a reactor in the manner shown in FIGS. 1 and 2, the electrode planes can be put together only in the manner which is shown in FIGS. 1 and 2 and in which conductive carrier elements alternate with insulating carrier elements on each end face since the edges, which come into engagement with one another, of adjacent carrier elements fit together only in this way. In the manner shown in FIG. 1, the recesses or projecting zones are of quadrangular shape. Of course, other corresponding shapes which produce asymmetry can also be selected instead.

The individual conductive carrier elements can be connected by means of leads 22 taken through the housing 1. Preferably, titanium wires are used for this purpose. In this way, only one passage to the outside is required, and this can be taken through at a point of the housing, which is particularly advantageous.

Figure 3:
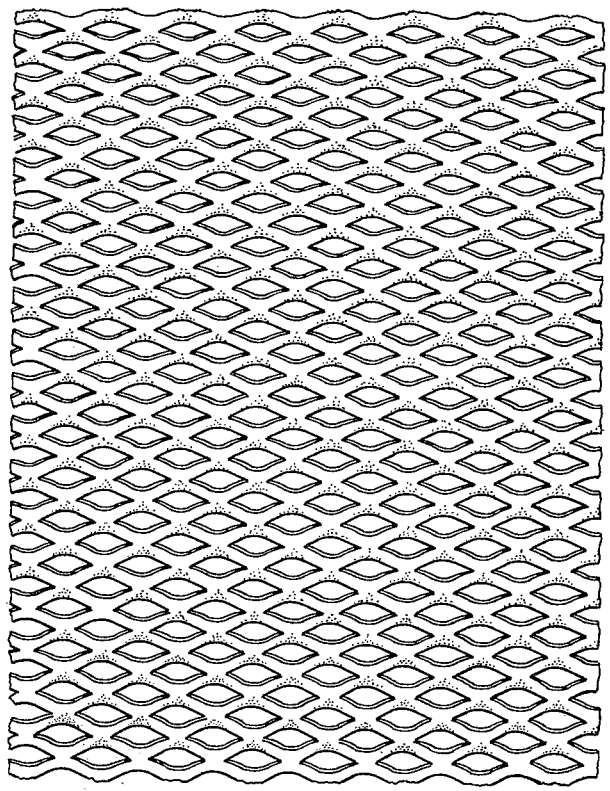
FIG. 3 is a perspective representation of a special form of electrode.
Figure 4:
FIG. 4 is a longitudinal section through the electrode shown in FIG. 3.
Figure 5:
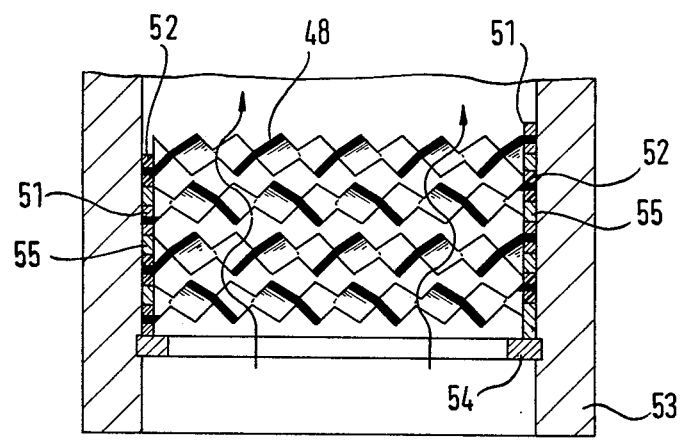
FIG. 5 shows a cross-section through the electrode shown in FIG. 3 when inserted into a housing.

FIGS. 3 to 5 show an embodiment employing, for the electrodes, non-rolled expanded metal. The material as such is shown in FIG. 3 in the form of a sheet metal panel of an appropriate conductive electrode material made by punching and subsequent longitudinal expansion under tension. A very large active surface is achieved with this electrode form and also by the three-dimensional shape resulting from the expansion. As a result of this three-dimensional shape, electrode surfaces 48 which are inclined relative to the horizontal can be produced, as can best be seen in FIG. 5. This inclined electrode form has the advantage that a very favourable removal of gas bubbles by the flow passing through is achieved.

On assembly of a reactor having the electrodes shown in FIGS. 3 and 4, the electrodes in successive planes are arranged with their directions of expansion offset by 180°. As a result, the zones which constitute the electrode surfaces 48 are inclined to the horizontal in one direction in one plane, and in the opposite direction in the next plane. Also, the surfaces 48 of the planes are laterally offset with respect to those in adjacent planes. These aspects of the construction can be seen in FIG. 5. A very long contact path between the liquid and the electrode surfaces is thus provided in the manner indicated by the arrows in FIG. 5 and, at the same time, good turbulence of the liquid is achieved. The electrode sheets are connected to a frame 51, 52 in the manner shown in FIG. 5. For assembly, they are simply inserted into a corresponding housing 53, the lowest frame being held on a holder ring 54. Spacers 55 are provided between individual frames. The electrode sheets are connected via the frames in the conventional manner to electric leads (not shown). The frames 51, 52 can be formed asymmetrically and are alternately conductive or non-conductive in the same way as described with reference to the embodiment of FIGS. 1 and 2, so that assembly is only possible in a manner determined by the geometrical form.

According to a further embodiment, the individual electrode planes are formed of a sintered material. The structure of this material is of a type in which metal beads, which are preferably made of titanium and preferably have a diameter in the range from about 0.5 to 3 mm, are heaped to a height of about 2 to 3 bead diameters and are metallically joined at the contact points by heating. The material formed in this way is set in frames on the sides, as in the preceding embodiments, and is inserted into a housing. A conductive connection is made as in the preceding embodiments and the frames can be formed asymmetrically in the same manner as described with reference to FIGS. 1 and 2 so that assembly is possible only in a predetermined way. The liquid passes through the spaces between the individual beads so that, on the one hand, a large contact surface is produced and, on the other hand, good turbulence takes place. Sintered materials formed in different ways can also be used as long as they have an adequate porosity which ensures, on the one hand, a large contact surface and, on the other hand, an adequate through-flow.

We claim:

1. A disinfection device comprising a housing defined by walls, and a plurality of electrodes arranged in planes, conductive carrier elements supporting and electrically interconnecting the elements of the planes at one end, non-conductive carrier elements supporting the elements of the plane at the other end, the conductive and non-conductive carrier elements being alternately provided along opposed walls of the housing, the edges of the conductive carrier elements having projecting zones with sides at an angle to the plane of the corresponding electrodes, the edges of the non-conductive carrier elements having recesses which correspond to and receive the projections on the conductive carrier elements.

2. A device according to claim 1 wherein the projections on first edges of the conductive carrier elements extends further from the centre lines of the electrodes than the projections on second edges of the conductive carrier elements.

3. A device according to claim 1 wherein the electrodes are made of expanded metal.

4. A device according to claim 3 wherein the direction of expansion of the metal is opposite in adjacent electrode planes.

5. A device according to claim 1 wherein the electrodes are made of sintered metal.

* * * * *